US010112015B2

(12) United States Patent
Seymour et al.

(10) Patent No.: US 10,112,015 B2
(45) Date of Patent: Oct. 30, 2018

(54) CONTINUOUS USE SYRINGE FILTER

(71) Applicant: GE HEALTHCARE UK LIMITED, Buckinghamshire (GB)

(72) Inventors: Geraint Seymour, Cardiff (GB); Martin David James, Cardiff (GB); Richard Martin West, Cardiff (GB)

(73) Assignee: GE HEALTHCARE UK LIMITED, Buckinghamshire (GB)

( * ) Notice: Subject to any disclaimer, the term of this patent is extended or adjusted under 35 U.S.C. 154(b) by 142 days.

(21) Appl. No.: 15/103,934

(22) PCT Filed: Nov. 26, 2014

(86) PCT No.: PCT/EP2014/075705
§ 371 (c)(1),
(2) Date: Jun. 13, 2016

(87) PCT Pub. No.: WO2015/090878
PCT Pub. Date: Jun. 25, 2015

(65) Prior Publication Data
US 2016/0317748 A1    Nov. 3, 2016

(30) Foreign Application Priority Data

Dec. 18, 2013   (GB) .................................. 1322408.4

(51) Int. Cl.
*A61M 5/31*      (2006.01)
*B01L 3/00*      (2006.01)
(Continued)

(52) U.S. Cl.
CPC .......... *A61M 5/3145* (2013.01); *A61M 5/165* (2013.01); *B01L 3/5635* (2013.01);
(Continued)

(58) Field of Classification Search
CPC ...... A61M 5/3145; A61M 5/31; A61M 5/178; B01L 3/5635; B01L 3/563; B01L 3/56; B01L 3/00
(Continued)

(56) References Cited

U.S. PATENT DOCUMENTS 3,938,513 A    2/1976   Hargest
4,066,079 A *  1/1978   Chiarolla ............... A61J 1/2096
                                                   604/190
(Continued)

FOREIGN PATENT DOCUMENTS

EP    0471721 A1    2/1992
EP    2695629 A2    2/2014
(Continued)

OTHER PUBLICATIONS

International Search Report and Written Opinion regarding International Application No. PCT/EP2014/075705, dated Feb. 3, 2015, 10 pages.
(Continued)

*Primary Examiner* — Christine T Mui
(74) *Attorney, Agent, or Firm* — Eversheds Sutherland (US) LLP (57) ABSTRACT

The present invention provides a device comprising: a housing comprising a first opening for connecting to a liquid source, a second opening for connecting with an apparatus for drawing in and expelling liquid, and a valve means comprising a filter carrier and a filter, the filter carrier supporting the filter and being movable within the housing; wherein the valve means permits liquid that is drawn into the housing from the liquid source by the apparatus to enter the apparatus by bypassing the filter but which forces liquid that
(Continued)

is subsequently pushed from the apparatus through the second opening into the housing to be filtered through the filter.

20 Claims, 7 Drawing Sheets

(51) Int. Cl.
*A61M 5/165* (2006.01)
*A61M 5/178* (2006.01)
*G01N 1/40* (2006.01)

(52) U.S. Cl.
CPC . *A61M 2005/3128* (2013.01); *A61M 2205/75* (2013.01); *B01L 2200/0631* (2013.01); *B01L 2300/0681* (2013.01); *B01L 2300/08* (2013.01); *B01L 2300/0858* (2013.01); *B01L 2300/12* (2013.01); *B01L 2400/06* (2013.01); *B01L 2400/0605* (2013.01); *G01N 2001/4088* (2013.01)

(58) Field of Classification Search
USPC ........... 436/177, 174; 422/546, 544, 500, 50
See application file for complete search history.

(56) References Cited

U.S. PATENT DOCUMENTS

| | | | |
|---|---|---|---|
| 4,229,306 A | 10/1980 | Hein et al. | |
| 4,366,822 A * | 1/1983 | Altshuler | A61B 10/025 600/566 |
| 6,217,540 B1 * | 4/2001 | Yazawa | G01N 33/491 604/4.01 |

FOREIGN PATENT DOCUMENTS

| | | | |
|---|---|---|---|
| GB | 2344526 A | 6/2000 | |
| WO | WO 90/13261 * | 11/1990 | A61B 10/00 |
| WO | 2012/138177 A2 | 10/2012 | |

OTHER PUBLICATIONS

GB Search Report regarding GB Application No. 1322408.4, dated Jun. 18, 2014, 3 pages.

\* cited by examiner

CONTINUOUS USE SYRINGE FILTER

CROSS-REFERENCE TO RELATED APPLICATIONS

This application is a filing under 35 U.S.C. 371 of international application number PCT/EP2014/075705, filed Nov. 26, 2014, which claims priority to GB application number 1322408.4, filed Dec. 18, 2013, the entire disclosures of each of which are hereby incorporated by reference.

FIELD OF THE INVENTION

The present invention relates to filtration devices and methods of using such devices to filter solutions.

BACKGROUND TO THE INVENTION

Filtration is a common method of separating larger particles in solution from smaller ones. Filters, filtrations devices and filtration methods are used in a wide range of biological and chemical applications for the separation or purification of various moieties.

Syringe filters are used in the art to filter liquids. Such filters are regularly used for the lab-scale filtration of liquids. The use of such filters typically comprises drawing the sample to be filtered into a syringe. The syringe is then attached to a syringe filter and the liquid is then pushed through the filter.

Often, when extracting a sample that requires filtration it is necessary to filter a volume of liquid larger than the volume of the syringe. In such circumstances, once the user has pushed the liquid from the syringe through the filter, the user would then have to remove the filter in order to draw up more of the (unfiltered) liquid sample into the syringe. The filter would then need to be replaced for the dispensing stage to ensure that the sample liquid is filtered. This process would need to be repeated until the full volume of liquid sample has been filtered. This can be time consuming and burdensome for the user. Furthermore, the need to move the syringe between filtration steps and to remove and re-attach the filter increases the risk of contamination of the solution to be filtered.

It would therefore be desirable to provide a filtration device that permits the user to draw in and filter a solution without having to change or remove the filter to refill the syringe. GE Healthcare have commercialised a filtration device, a Clyde in-line filter, through its WHATMAN™ (laboratory separations products) portfolio. The CLYDE™ (in-line filter sterilizer) device is a single device system comprising a sample inlet pipe, a one-way valve, a flat filter, a syringe and connecting pipework. The device permits a user to filter up to 2 L of solution in a continuous process. The device can be built with a limited number of available filters.

However, there is a continuing need in the art to provide alternative forms of such "one way" filters that can be manufactured on a large scale from readily available, cost-effective materials and which are simply and easy to operate by a user—typically a lab researcher or technician.

SUMMARY OF THE INVENTION

According to a first aspect of the present invention, there is provided a device comprising:

a housing comprising a first opening for connecting to a liquid source, a second opening for connecting with an apparatus for drawing in and expelling liquid, and a valve means comprising a filter carrier and a filter, the filter carrier supporting the filter and being movable within the housing;

wherein the valve means permits liquid that is drawn into the housing from the liquid source by the apparatus to enter the apparatus by bypassing the filter but which forces liquid that is pushed from the apparatus through the second opening into the housing to be filtered through the filter.

In one embodiment, the apparatus for taking in and expelling liquid is a syringe or a pipette.

In a further embodiment, the first opening forms a valve seat with the housing, and the filter carrier is forced away from the valve seat when liquid is drawn into the apparatus to create a liquid path between the first and second openings that bypasses the filter, and is pushed against the valve seat to remove the liquid path when liquid is expelled from the apparatus.

In a further embodiment, the housing comprises opposed spaced apart first and second walls, optionally separated by a side wall, and wherein the first opening is formed on the first wall and the second opening is formed on the second wall. The valve seat is preferably formed from the first wall and the first opening.

In a further embodiment, the filter carrier comprises a base portion, the base portion comprising a filter outlet to permit filtered liquid to exit the carrier. The base portion preferably supports, at least in part, the filter. The base portion of the filter carrier can be pushed against the first wall of the housing when liquid is pushed from the apparatus so that liquid pushed from the apparatus through the second opening must be filtered by passing through the filter. In a further embodiment, the first opening of the housing and the filter outlet of the base portion of the filter carrier are formed by conduits extending from the respective first wall of the housing and the base portion of the filter carrier, and at least a portion of the length of the conduit extending from the base portion of the filter carrier projects into the conduit extending from the first wall of the housing when the base portion is pushed against the first wall of the housing. In a yet further embodiment, the first wall of the housing comprises an inner face and the base portion of the filter carrier comprises an outer face, and the respective inner and outer faces comprise matched parallel faces. The first wall of the housing and the base portion of the filter carrier may be substantially conical in shape.

In a further embodiment, the housing comprises one or more projecting members that abut with the filter carrier and/or the filter when liquid is being drawn into the apparatus, thereby ensuring that the second opening is not sealed by the movement of the filter carrier or filter as liquid is being drawn into the apparatus. In a further embodiment, the second wall of the housing comprises an inner face, and the inner face comprises one or more of such projecting members that abut with the filter carrier and/or the filter when liquid is being drawn into the apparatus, thereby ensuring that the second opening is not sealed by the movement of the filter carrier or filter as liquid is being drawn into the apparatus. The projecting members may comprise a plurality of ribs extending radially from the second opening. In a further embodiment, the housing comprises opposed spaced apart first and second walls separated by a side wall, and the ribs further extend down the inner surface of the side wall. The ribs on the inner surface of the side wall can guide the movement of the filter carrier to ensure the horizontal surface of the filter is maintained in a plane that is substantially perpendicular to the direction of the side wall.

In a further embodiment, the filter comprises one or more membrane filters. In a further embodiment, the housing is made of a plastic material.

The apparatus for drawing in and expelling liquid (typical a syringe or pipette) can be attached by the user to the device. Alternatively, the apparatus can be pre-attached to the device in a permanent or readily detachable form. Accordingly, in a second aspect of the present invention, there is provided a housing comprising a first opening for connecting to a liquid source, a second opening connected to an apparatus for drawing in and expelling liquid, and a valve means comprising a filter carrier and a filter, the filter carrier supporting the filter and being movable within the housing; wherein the valve means permits liquid that is drawn into the housing from the liquid source by the apparatus to enter the apparatus by bypassing the filter but which forces liquid that is subsequently pushed from the apparatus through the second opening into the housing to be filtered through the filter.

The valve means, housing, filter and filter carrier of the second aspect of the invention may have the features described in any of the embodiments described above with respect to the first aspect of the invention.

In a further aspect of the present invention, there is provided a method of filtering a liquid using a device of the present invention.

By providing a device described above, a user can, by hand, draw sample from a bulk solution and dispense the drawn sample through the filter in a continuous fashion without the need to remove the filter in the event that the housing (e.g. syringe or pipette) cannot accommodate the full volume of liquid that is to be filtered. Furthermore, the device provides a low cost component to a filtering application within the laboratory. The syringe or pipette can be attached by the user to the device of the first aspect of the invention. Alternatively, the syringe or pipette can be attached to the device in a permanent or detachable form. The device can be used with syringes or pipettes from any supplier with a compatible connection such as a compatible standardised luer connection.

DETAILED DESCRIPTION OF THE INVENTION

According to a first aspect of the present invention, there is provided a housing comprising a first opening for connecting to a liquid source, a second opening for connecting with an apparatus for drawing in and expelling liquid, and a valve means comprising a filter carrier and a filter, the filter carrier supporting the filter and being movable within the housing; wherein the valve means permits liquid that is drawn into the housing from the liquid source by the apparatus to enter the apparatus by bypassing the filter but which forces liquid that is subsequently pushed from the apparatus through the second opening into the housing to be filtered through the filter.

Figure 1A:
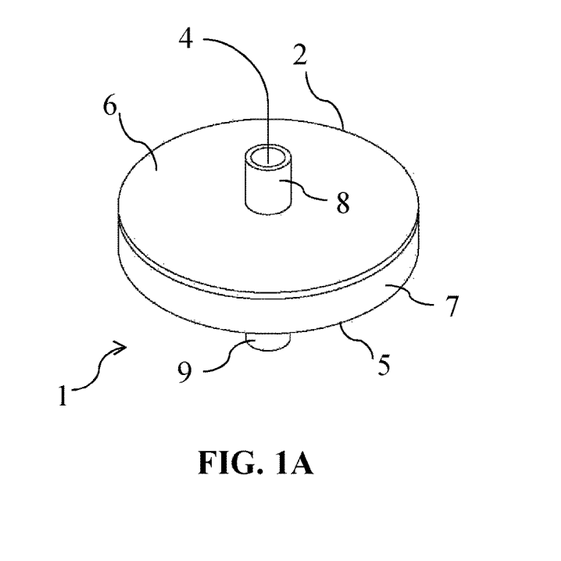
FIG. 1A is a three dimensional schematic of a device according to the present invention.
Figure 1B:
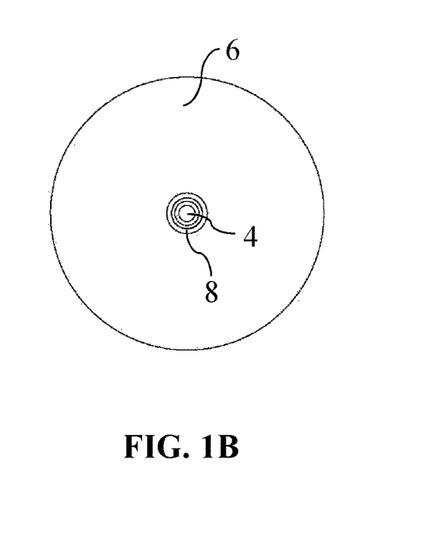
FIG. 1B is a plan view of the device of FIG. 1A when viewed from above the device of FIG. 1A.
Figure 1C:
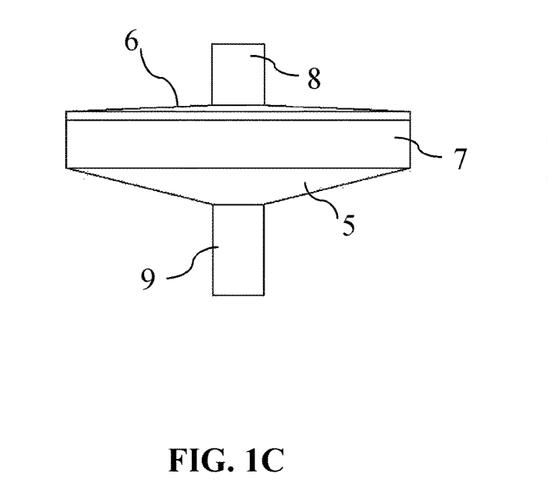
FIG. 1C is a side view of the device of FIG. 1A.
Figure 1D:
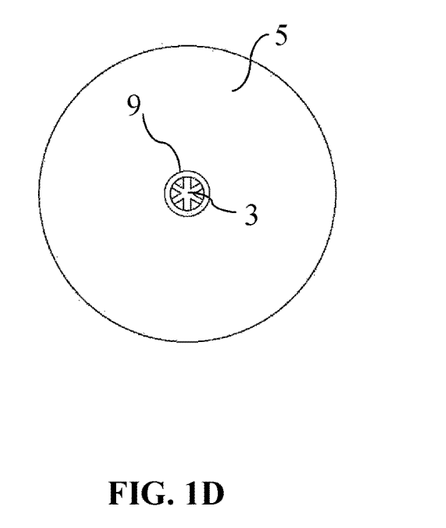
FIG. 1D is a plan view when viewed from below the device of FIG. 1A.

FIGS. 1A and 1C are three dimensional schematics showing a preferred embodiment of the present invention. FIGS. 1B and 1D are respective top and bottom plan views. The device 1 comprises a housing 2. The housing comprises a first opening 3 for connecting to a liquid source and a second opening 4 for connecting to an apparatus for drawing in and expelling liquid through the second opening. The apparatus may be, for example, a syringe or a pipette apparatus. In a particularly preferred embodiment, the apparatus is a syringe.

The housing of the device of the present invention will typically comprise opposed spaced apart first and second walls, optionally separated by a side wall, with the first opening present on the first wall and the second opening present on the second wall. In FIG. 1, the first wall 5 and the second wall 6 are separated by a side wall 7. The first or second walls of the housing, preferably both, will typically have fitting members that may take the forms of tubular channels or conduits 8, 9 extending from the respective first and second openings, thereby providing channels through which liquid can enter and exit the housing via the openings. The housing will typically provide a water-tight enclosure such that the liquid (e.g. water) can only enter and exit the housing via the openings. Accordingly, the housing should be constructed from a water impermeable material, for example, a plastic material such as, but not limited to, polypropylene.

One or both of the fitting members may provide luer-type and/or tapered fitting connection points to permit easy to-use, liquid-tight connection points. Such fittings are well known in the art. The fitting connection associated with the second inlet may comprise a male or female fitting to allow for a water-tight seal with the corresponding other of the male or female fitting present on the apparatus (e.g. a syringe or pipette). The fitting associated with the first inlet may comprise a male or female fitting to allow for a water-tight seal with a pipette tip or the like to facilitate the drawing of liquid from the bulk liquid source into the housing.

The valve means of the present invention permits liquid that is drawn into the housing from the liquid source by the apparatus to enter the apparatus by bypassing the filter. The term bypassing the filter means that the liquid source can be drawn into the apparatus efficiently without passing through the filter itself. Furthermore, the liquid can be drawn into the apparatus by the user easily despite the presence of the filter carrier in the housing. Furthermore, the valve functions to force liquid that is subsequently pushed from the apparatus through the second opening into the housing to be filtered through the filter. In this way, liquid can be drawn into the apparatus and then filtered through the filter multiple times without having to physically separate the apparatus (e.g. syringe) from the filter.

In a preferred embodiment of the present invention, the first opening of the housing forms a valve seat with the housing, and the filter carrier is forced away from the valve seat when liquid is drawn into the apparatus to create one or more liquid paths between the first and second opening that bypass the filter, and is pushed against the valve seat to remove the liquid path when liquid is expelled from the apparatus.

Figure 2:
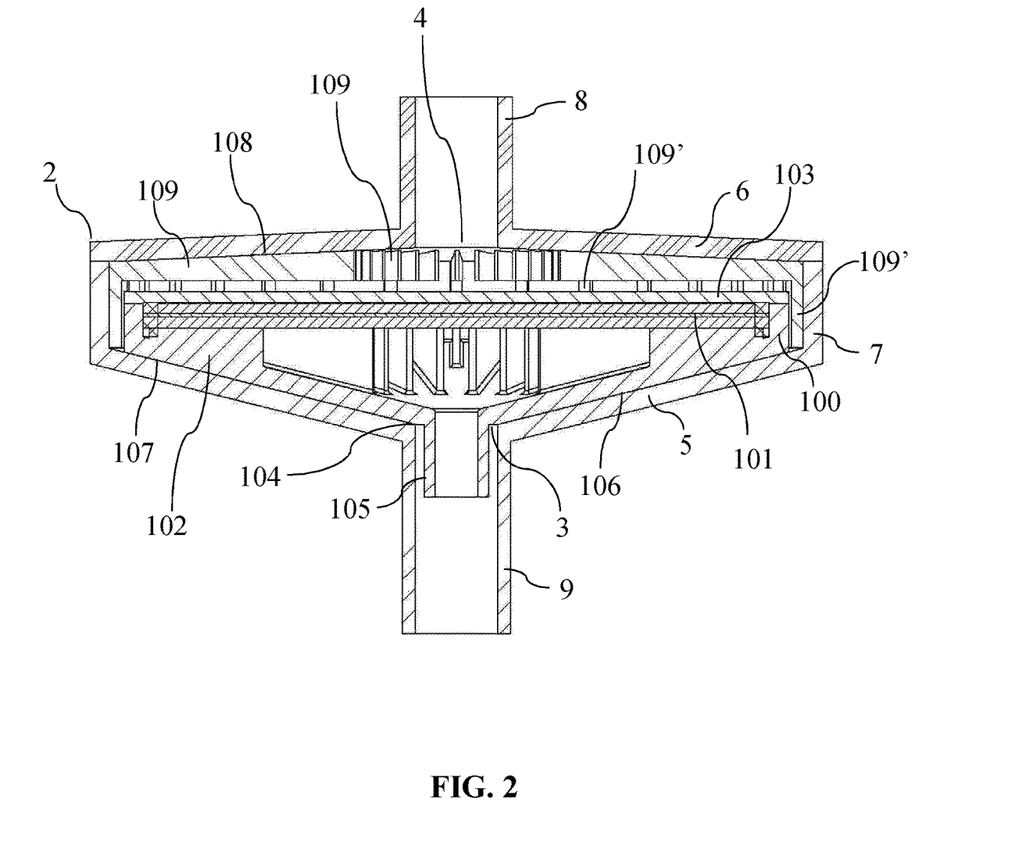
FIG. 2 is a sectional view of a device according to the present invention.

FIG. 2 shows a sectional view of a device according to the present invention. The device shown in FIG. 2 provides an example of how the valve can be incorporated into the housing. The valve comprises a filter carrier 100 which supports the filter 101. The filter carrier may further comprise a filter carrier lid 103 that serves to help affix the filter to the filter carrier. The filter carrier lid 103 may comprise a one or more cavities or gaps (not shown) to permit liquid to contact the filter when it is pushed through the inlet 4. The filter carrier is movable such that it can move, typically in the vertical direction, towards (and occupy) the valve seat 104 and also move away from the valve seat 104. The valve seat 104 is created by the housing and the first opening 3.

The filter carrier is configured such that liquid passing through the filter into the filter carrier passes through the outlet 105 of the filter carrier. Accordingly, the filter carrier preferably provides a liquid or water-tight seal beneath the filter between the filter and the outlet. The filter carrier outlet 105 will typically be formed by a tubular channel or conduit extending from base portion 102 and being in fluid communication with the inside of the filter carrier, thereby providing a channel through which liquid can exit the filter carrier after passing through the filter 101. At least a portion of the tubular channel or conduit 105 may project or extend into the conduit 9 extending from the first wall 5 of the housing 2, thereby ensuring that liquid dispensed out of the filter carrier exits the housing 2 in the direction of the conduit 9.

The filter carrier 100 comprises a base portion 102 beneath the filter 101. The outlet 105 described above is formed at the base of the base portion 102. The base portion 102 comprises an outer face or surface 107 which is opposed to the inner face or surface 106 of the first wall 5 of the housing 2. The term "surface" and "face" are used interchangeably herein. In a preferred embodiment, the respective inner and outer faces 106 and 107 together form matched parallel faces. The term "matched parallel faces" is used to describe the scenario wherein, at any given point on the opposed faces, the opposed faces are parallel. This permits the filter carrier and the housing to form a liquid-tight seal at the valve seat 104 when the filter carrier is pushed in the direction of the first face of the housing. This can be achieved when respective portions of the filter carrier and the housing have complementary shapes that fit flush against one another. In a preferred embodiment, the first wall 5 of the housing and the base portion of the filter carrier 102 are substantially conical in shape. In a further embodiment, the respect inner and outer faces 106 and 107 are substantially conical in shape. In this way, the respective inner and outer faces 106 and 107 together formed matched parallel faces. However, it will be appreciated that other shapes can be used to achieve the same effect.

The second surface 6 of the housing comprises an inner face or surface 108 which faces the surface of the filter 101. The inner face 108 may comprise one or more projecting members that abut with the filter carrier and/or filter when the filter carrier is moved towards the second opening 4 of the housing. The projecting member(s) thereby function to prevent the filter carrier and/or filter from blocking the second opening 4 of the housing. The projecting members may be in the form of a plurality of ribs 109, which may extend radially from second opening. The ribs 109 can thereby function not only to prevent the filter carrier and/or filter from blocking the second opening 4 of the housing but also provide liquid passages for the liquid that is pulled into the syringe or pipette. The ribs may also extend down the inner surface of the side wall 7 of the housing as denoted by the numeral 109' in FIG. 2. In this way, the ribs 109' also serve as support member to ensure the filter carrier only moves in the vertical direction, up or down, within the housing between the first and second inlet. The movement of the filter carrier is preferably guided such that the horizontal surface (the surface facing the second opening) is maintained in a plane that is substantially perpendicular to the direction of the side wall.

It will be appreciated that the projecting members described above need not necessarily have the form described above, as long as the projecting members abut with the filter carrier and/or the filter when liquid is being drawn into the apparatus, thereby ensuring that the second opening is not sealed by the movement of the filter carrier or filter as liquid is being drawn into the apparatus.

Figure 3:
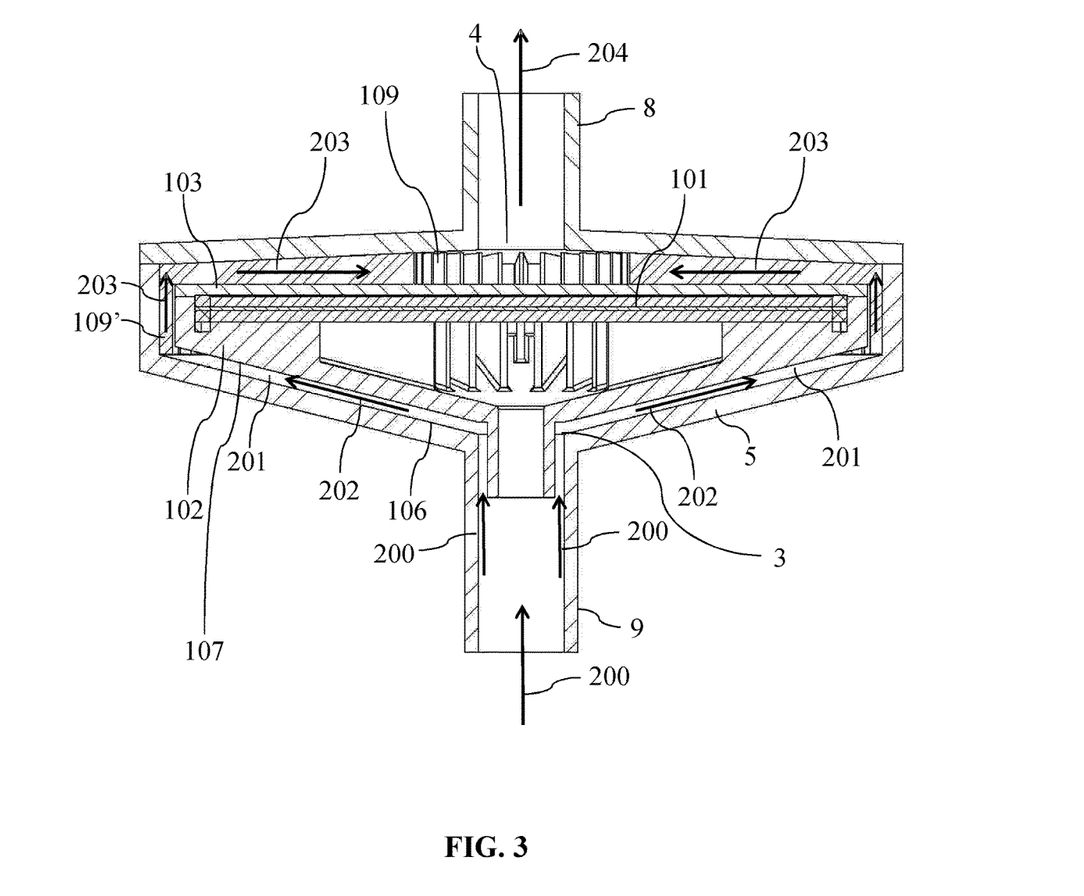
FIG. 3 is a sectional view of a device according to the present invention when liquid is being drawn from a liquid source into a syringe (the syringe is not shown).

FIG. 3 is a sectional view of a device according to the present invention when liquid is being drawn from a liquid source into a syringe. The syringe (not shown) is in fluid communication with the second inlet 4 of the housing and will typically be attached to the housing via the conduit 8. The first inlet 3 will be connected to a liquid source (the liquid to be filtered). This could be via pipette tip attached the tubular projection 9 extending from the first inlet. Alternatively, the second inlet could be in in direct contact with the liquid source.

With reference to FIG. 3, as the syringe is actuated to draw liquid into the syringe (e.g. by pulling back the piston within the syringe), the filter carrier 101 rises. As the filter carrier rises, the filter carrier moves away from the first wall 5 of the housing. This creates gap 201 between the base portion of the filter carrier 102 and the first wall 5 of the housing. Liquid that is drawn into the housing (denoted by arrows 200) can then flow through the gap 201, as indicated by arrows 202.

The movement of the filter carrier is restricted by the ribs 109 and 109' which provide liquid passages, thereby allowing liquid that is drawn into gap 201 to flow to the inlet 4, as denoted by arrows 203. The liquid then enters the syringe as denoted by arrow 204. When the user draws liquid into the syringe it will not enter the outlet of the filter carrier and the inside of the filter carrier because the resistance is higher at this part due to the presence of the filter (which may, e.g. be in the form of one or more filter membranes) than it is for the space 201 created between the filter carrier and the housing.

Figure 4:
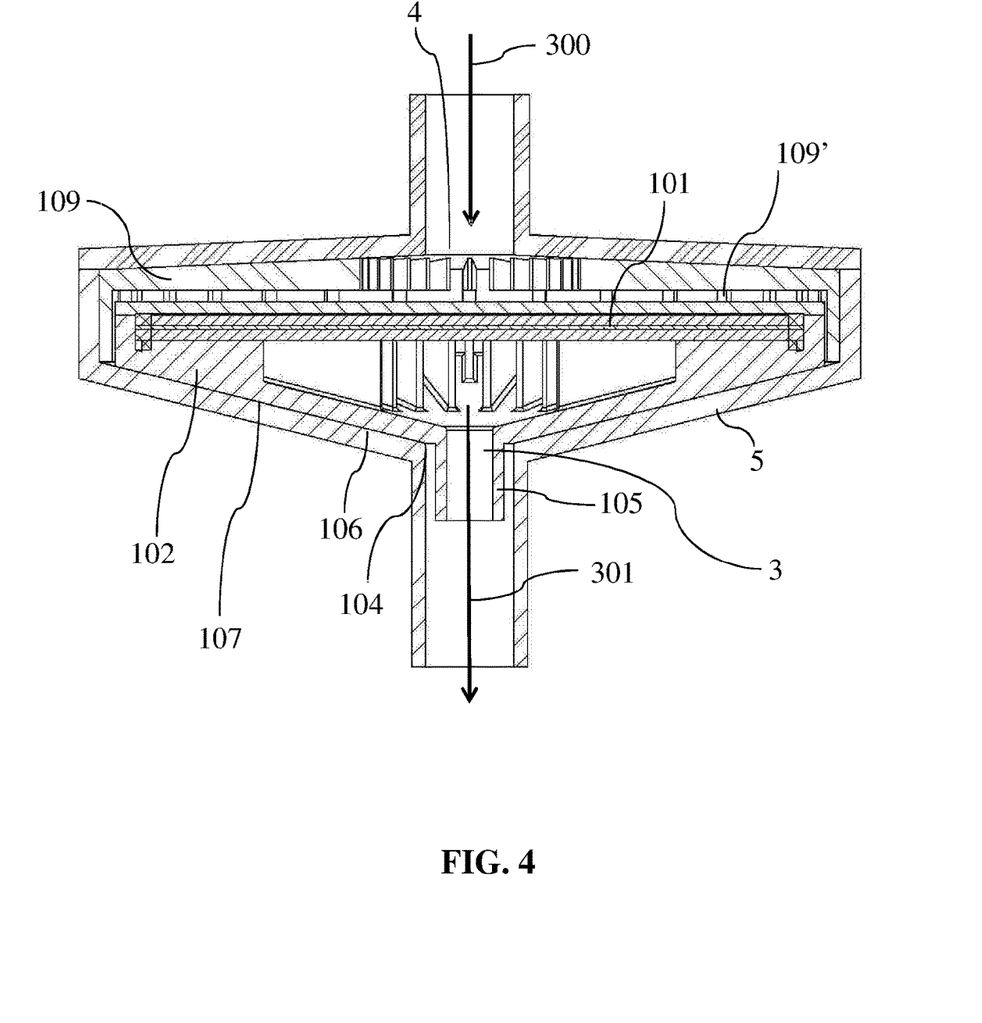
FIG. 4 is a sectional view of a device according to the present invention when liquid is being pushed from the syringe (not shown) and through the filter.

FIG. 4 is a sectional view of a device according to the present invention when liquid is being pushed from the syringe and through the filter. The syringe (not shown) will have been filled as described in FIG. 3. When the user pushes liquid from the syringe (e.g. by pushing in the piston of the syringe) into the second opening 4 of housing (denoted by the arrow 300), the filter carrier is forced towards the valve seat 104. When the filter reaches and occupies the valve seat 104, the gap 201 (shown in FIG. 3) between the outer face 107 of the base portion of the filter carrier and the inner face 106 of the first wall of the housing is closed. This has the effect of closing the liquid path followed by the liquid in FIG. 3 which permitted the liquid to bypass the filter 101. Instead, the movement of the filter carrier to close the gap 201 forces the liquid to pass through the filter 101 and out of the first opening 3 of the housing (as denoted by arrow 301). As the liquid is filtered, the pressure will increase with time as particles become trapped within the filter. This enables a tight seal to exist and prevents leakage between the seal created by the abutment of the base portion of the filter carrier and the housing, thus preventing the formation of gap 201.

A typical workflow for the device is for the user to pull liquid into the syringe (or whichever apparatus is employed to draw and expel liquid) from a vessel containing liquid to be filtered and then for the user to move the device (with the syringe attached) to a different vessel before pushing the liquid through the filter. The user will then move across to the unfiltered liquid vessel and draw a new volume into the same syringe and filter as before by moving across to the vessel where the filtrate is to be placed. This process can be repeated until the volume of material has been filtered or if a drop off in performance is detected and a new filter is required to complete the operation.

The filter may comprise a flat or membrane filter. The filter will separate wanted (or unwanted) particles in the liquid from the remainder of the liquid (the filtrate). The filtrate then leaves the filter and can be collected in a suitable receptacle. Multiple types of filters and filter elements may be used in the present invention. In a preferred embodiment, the filter element comprises one or more filter membranes. Suitable materials for such filter elements, such as filter membranes, include polytetrafluoroethylene (PTFE), polypropylene, regenerated cellulose (RC), polyvinylidene fluoride (PVDF), Nylon, or Glass fibre. Pore sizes typically range from 0.1 μm to 0.7 mm but can be outside of this window. The thickness of the filter element can vary greatly, typically ranging from 0.05 um to around 0.25 mm.

In a further embodiment of the present invention, the housing of the device may have a further inlet to allow liquid to be drawn into the housing via one inlet and to be expelled from the housing via a different inlet (rather than having a single opening functioning as both an inlet and an outlet). This would mean that the liquid paths within the device would differ but the device operation would be the same.

Figure 5A:
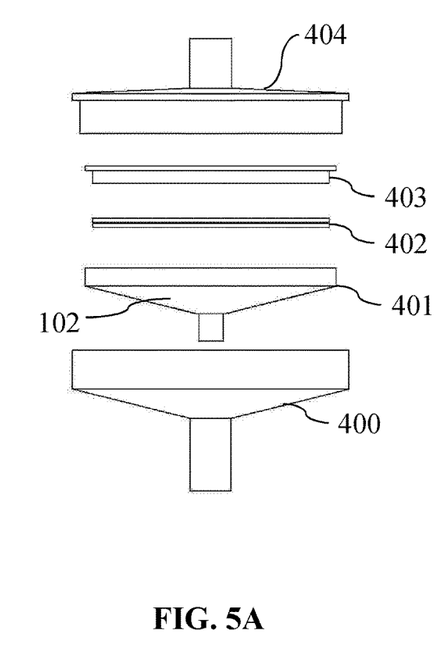
FIG. 5A is a schematic showing how a device according to the present invention can be constructed from component parts.
Figure 5B:
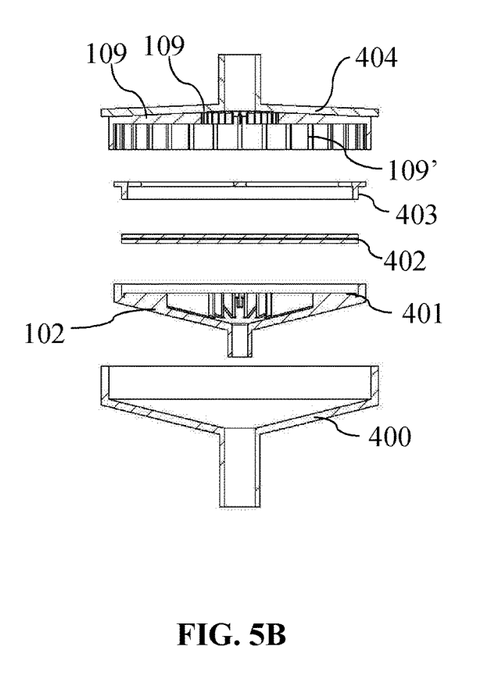
FIG. 5B is a sectional view of the component parts shown in FIG. 5A.

FIGS. 5A and 5B show how a device according to the present invention can be constructed from component parts. The device can be constructed by first placing a filter membrane or membrane stack 402 into a filter carrier base 401 comprising a base portion 102. A filter carrier lid 403 is placed on top of the filter membrane which may be ultrasonically welded into place. The assembled filter carrier is then placed inside the base of the housing 400 comprising the first opening. The top part 404 of the housing comprising the second opening can then be ultrasonically welded onto the base to create a liquid tight housing comprising the filter carrier.

Figure 6:
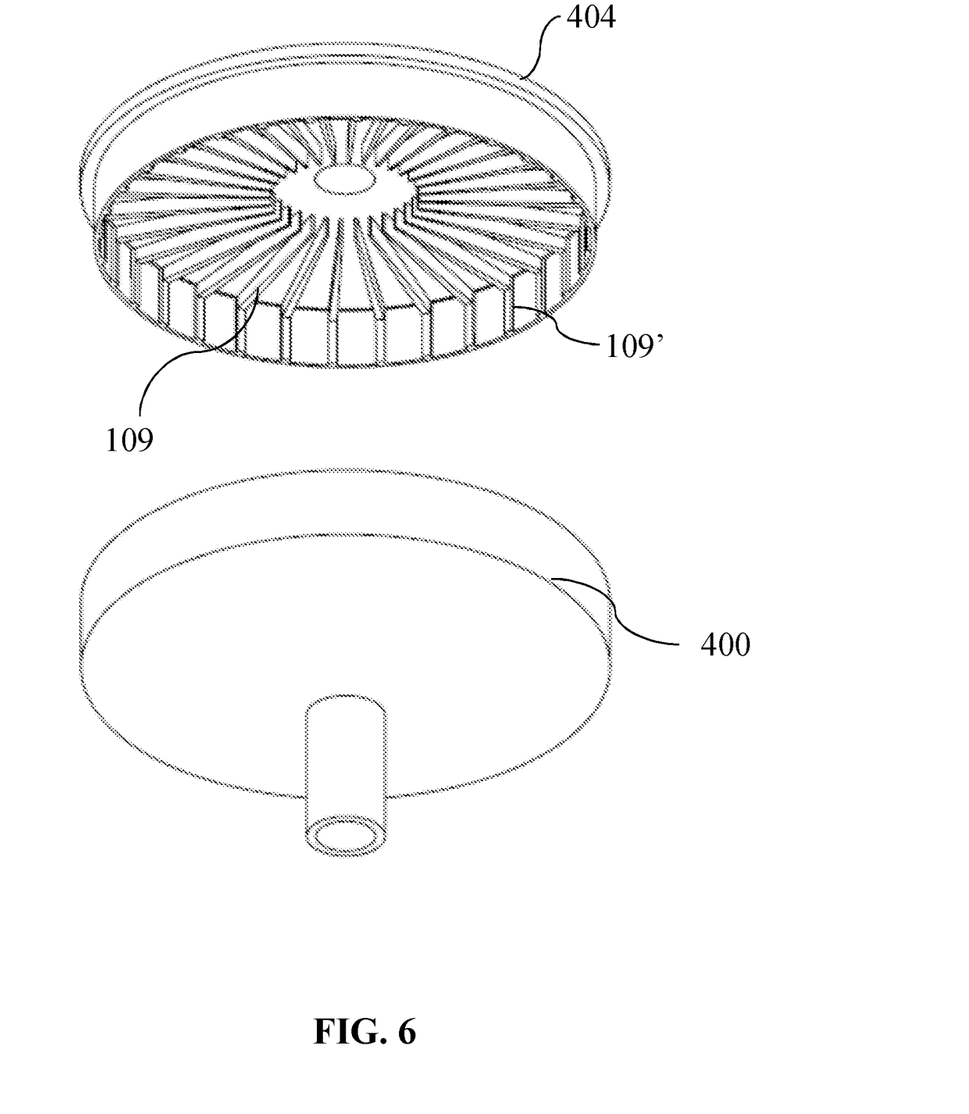
FIG. 6 provides a three dimensional schematic of lower and upper portions of a housing of a device according to the present invention which can be welded together to create a housing.
Figure 7:
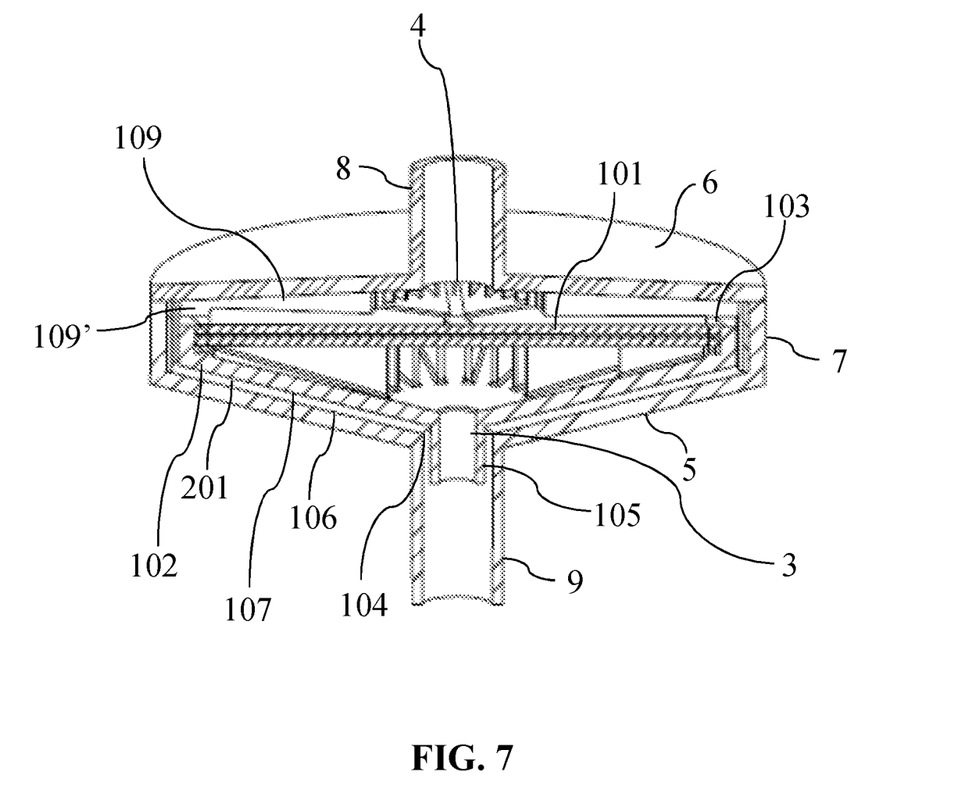
FIG. 7 provides a three dimensional schematic transverse sectional view of a device according to the present invention.

FIG. 6 provides a three dimensional schematic of the base of the housing 400 and the top part of the housing 404 shown in FIGS. 5A and 5B.

The housing and/or the filter carrier can be made from a number of materials. The materials used will preferably be impermeable to water or the liquid to be filtered. In a preferred embodiment, the housing and/or the filter carrier is made from a plastic material that is suitable for laboratory use. Typically, the plastic would be polypropylene, but other plastics could also be employed. The component parts may be injection moulded from polypropylene (or other suitable plastics) such that the device can be manufactured as a low cost disposable item and therefore used as a hand-held device.

The apparatus for withdrawing and expelling the liquid to be filtered can be permanently fixed to the housing containing the filter carrier. Alternatively, the housing containing the filter carrier can be reversibly attached to the apparatus to permit the device to be used with multiple different syringe or pipette types selected by the user.

The invention claimed is:

1. A device comprising:
a housing comprising a first opening for connecting to a liquid source, a second opening for connecting with an apparatus for drawing in and expelling liquid, ribs extending down an inner surface of the housing, and a valve means comprising a filter carrier and a filter, the filter carrier supporting the filter and being movable within the housing, such that movement of the filter is constrained to movement of the filter carrier;
wherein the ribs continuously constrain movement of the filter carrier and the filter to a vertical direction, and wherein the valve means permits liquid that is drawn into the housing from the liquid source by the apparatus to enter the apparatus by bypassing the filter but which forces liquid that is pushed from the apparatus through the second opening into the housing to be filtered through the filter.

2. A device according to claim 1, wherein the apparatus for taking in and expelling liquid is a syringe or a pipette.

3. A device according to claim 2, wherein first opening forms a valve seat with the housing, and wherein the filter carrier is forced away from the valve seat when liquid is drawn into the apparatus to create a liquid path between the first and second openings that bypasses the filter, and is pushed against the valve seat to remove the liquid path when liquid is expelled from the apparatus.

4. A device according to claim 3, wherein the housing comprises opposed spaced apart first and second walls, optionally separated by a side wall, and wherein the first opening is formed on the first wall and the second opening is formed on the second wall.

5. A device according to claim 4, wherein the first wall and first opening form the valve seat.

6. A device according to claim 5, wherein the filter carrier comprises a base portion, the base portion comprising a filter outlet to permit filtered liquid to exit the carrier.

7. A device according to claim 6, wherein the base portion of the filter carrier is forced against the first wall of the housing when liquid is pushed from the apparatus so that liquid pushed from the apparatus through the second opening must be filtered by passing through the filter.

8. A device according to claim 7, wherein the first opening of the housing and the filter outlet of the base portion of the filter carrier are formed by conduits extending from the respective first wall of the housing and the base portion of the filter carrier, and wherein at least a portion of the length of the conduit extending from the base portion of the filter carrier projects into the conduit extending from the first wall of the housing when the base portion is pushed against the first wall of the housing.

9. A device according to claim 8, wherein the first wall of the housing comprises an inner face and the base portion of the filter carrier comprises an outer face, and wherein the respective inner and outer faces comprise matched parallel faces.

10. A device according to claim 9, wherein the first wall of the housing and the base portion of the filter carrier are substantially conical in shape.

11. A device according to claim 10, wherein the second wall of the housing comprises an inner face, and wherein the inner face comprises one or more projecting members that abut with the filter carrier and/or the filter when liquid is being drawn into the apparatus, thereby ensuring that the second opening is not sealed by the movement of the filter carrier or filter as liquid is being drawn into the apparatus.

12. A device according to claim 11, wherein the projecting members comprise a plurality of ribs extending radially from the second opening.

13. A device according to claim 12, wherein the housing comprises opposed spaced apart first and second walls separated by a side wall, and wherein the ribs further extend down the inner surface of the side wall.

14. A device according to claim 13, wherein the ribs on the inner surface of the side wall guide the movement of the filter carrier to ensure the horizontal surface of the filter is maintained in a plane that is substantially perpendicular to the direction of the side wall.

15. A device according to claim 14, wherein the filter comprises one or more membrane filters.

16. A device according to claim 15, wherein the housing is made of plastic.

17. A device according to claim 1, wherein first opening forms a valve seat with the housing, and wherein the filter carrier is forced away from the valve seat when liquid is drawn into the apparatus to create a liquid path between the first and second opening that bypasses the filter, and is pushed against the valve seat to remove the liquid path when liquid is expelled from the apparatus.

18. A method of filtering a sample liquid, the method comprising:
(a) providing a device as claimed in claim 16;
(b) attaching an apparatus for taking in and expelling liquid to the second opening;
(c) operating the apparatus to draw in sample liquid through the first opening and into the apparatus;
(d) operating the apparatus to push sample liquid from the apparatus back through the second opening and into the filter.

19. A method of filtering a sample liquid, the method comprising:
(a) providing a device as claimed in claim 17;
(b) attaching an apparatus for taking in and expelling liquid to the second opening;
(c) operating the apparatus to draw in sample liquid through the first opening and into the apparatus;
(d) operating the apparatus to push sample liquid from the apparatus back through the second opening and into the filter.

20. Use of a device as defined in claim 17 for filtering a liquid.

* * * * *